United States Patent
Nagaki et al.

(10) Patent No.: US 8,710,281 B2
(45) Date of Patent: Apr. 29, 2014

(54) CATALYSTS FOR HYDRODEOXYGENATION OF POLYOLS

(75) Inventors: Dick Alan Nagaki, The Woodlands, TX (US); Randy D. Cortright, Madison, WI (US); Lisa Kamke, Madison, WI (US); Elizabeth Woods, Middleton, WI (US)

(73) Assignee: Virent, Inc., Madison, WI (US)

( * ) Notice: Subject to any disclaimer, the term of this patent is extended or adjusted under 35 U.S.C. 154(b) by 584 days.

(21) Appl. No.: 12/980,892

(22) Filed: Dec. 29, 2010

(65) Prior Publication Data

US 2011/0160482 A1 Jun. 30, 2011

Related U.S. Application Data

(60) Provisional application No. 61/291,050, filed on Dec. 30, 2009.

(51) Int. Cl.
*C07C 29/156* (2006.01)
*C07C 29/136* (2006.01)

(52) U.S. Cl.
USPC ........................................................ 568/903

(58) Field of Classification Search
USPC ........................................................ 568/903
See application file for complete search history.

(56) References Cited

U.S. PATENT DOCUMENTS

2008/0025903 A1  1/2008  Cortright

FOREIGN PATENT DOCUMENTS

WO  2008077205 A1  7/2008
WO  2009129256 A1  10/2009

OTHER PUBLICATIONS

International Search Report PCT/US2010/062346 mailed Jul. 26, 2011.

*Primary Examiner* — Elvis O Price
(74) *Attorney, Agent, or Firm* — Quarles & Brady LLP

(57) ABSTRACT

Disclosed are methods for producing polyols, ketones, carboxylic acids, aldehydes and alcohols from biomass-derived oxygenated hydrocarbons, such as sugars, sugar alcohols, saccharides and the like, using catalysts containing platinum, ruthenium and tin. The methods can be run at lower temperatures and pressures, and allows for the production of oxygenated compounds without the need for hydrogen from an external source. The oxygenated compounds produced are useful as industrial chemicals or chemical intermediates for liquid fuels production.

18 Claims, 12 Drawing Sheets

Figure 5. Catalytic performance of MRuSn-ZrO$_2$ (M=Pt, Re). Reaction conditions: glycerol=50%, T=220C, P=682 psi, WHSV=1 hr$^{-1}$, H$_2$/glycerol ratio=2.46.

Figure 5. Catalyst selectivity of MRuSn/ZrO$_2$ catalysts. Reaction conditions: glycerol=50%, T=220C, P=682 psi, WHSV=1 hr$^{-1}$, H$_2$/glycerol ratio=2.46.

Figure 7. MRuSn/ZrO$_2$ catalyst performance H$_2$ vs APR feed stream. Reaction conditions: glycerol=50%, T=220C, P=682 psi, WHSV=1 hr$^{-1}$, H$_2$/glycerol ratio=2.46.

Figure 8. Product Distribution for APR-HDO System

Figure 9. Product Distribution for APR-HDO System – Major Components

Figure 10. Product Distribution for APR-HDO System - Byproducts

Figure 11: Product Distribution for PtRuSn/W-ZrO2 catalyst using 50% Corn Syrup Feed

CATALYSTS FOR HYDRODEOXYGENATION OF POLYOLS

CROSS-REFERENCE TO RELATED APPLICATIONS

This application claims priority to U.S. Provisional Patent Application No. 61/291,050, filed Dec. 30, 2009.

FEDERAL FUNDING STATEMENT

This invention was made with government support under Grant No 2009-10002-05122 awarded by the United States Department of Agriculture. The government has certain rights in this invention.

TECHNICAL FIELD

The present invention is directed to catalysts and their use in the conversion of sugars, sugar alcohols and other carbohydrates to lower molecular weight oxygenated compounds, such as polyols, alcohols, ketones, aldehydes and carboxylic acids.

BACKGROUND

Increasing cost of fossil fuel and environmental concerns have stimulated worldwide interest in developing alternatives to petroleum-based fuels, chemicals, and other products. Biomass (material derived from living or recently living biological materials) is one category of possible renewable alternative to such fuels and chemicals.

A key challenge for promoting and sustaining the use of biomass in the industrial sector is the need to develop efficient and environmentally benign technologies for converting biomass to useful products. A number of biomass conversion technologies unfortunately tend to carry additional costs which make it difficult to compete with products produced through the use of traditional resources, such as fossil fuels. Such costs often include capital expenditures on equipment and processing systems capable of sustaining extreme temperatures and high pressures, and the necessary operating costs of heating fuels and reaction products, such as fermentation organisms, enzymatic materials, catalysts and other reaction chemicals.

One promising technology is the BioForming® platform being developed by Virent Energy Systems, Inc. The BioForming platform is based on the combination of aqueous phase reforming (APR) and/or hydrodeoxygenation with conventional catalytic processing technologies, including acid condensation, base catalyzed condensation, acid catalyzed dehydration, and/or alkylation. In its operation, soluble carbohydrates extracted from biomass are introduced into a BioForming reactor with water as an aqueous feedstock. The aqueous carbohydrate feedstock is then converted into reactive intermediates through one or more APR/hydrodeoxygenation reactions. Once formed, the chemical intermediates undergo further catalytic processing to generate hydrocarbons for gasoline, jet fuel, diesel, or chemicals. Other aspects of the BioForming process are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); U.S. Pat. No. 7,767,867 and U.S. patent application Ser. No. 12/834,306 (to Cortright, and entitled "Methods and Systems for Generating Polyols"); U.S. Patent Application Ser. Nos. 2008/0216391; 2008/0300434; and 2008/0300435 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

One key step in the BioForming process is the ability to convert water soluble carbohydrates at moderate temperatures and pressures to produce intermediate compounds for further processing or use in the industry. To be commercially effective, however, the process must be able to convert the carbohydrate feedstock to the necessary compounds at yields that are economical as compared to other technologies. The process must also effectively remove oxygen from the carbohydrate without a significant disruption of the corresponding carbon backbone.

Researchers have recently developed methods to react pure hydrogen with larger biomass-derived polyols (glycerol, xylitol, and sorbitol) and sugars (xylose and glucose) over hydrogenation and hydrogenolysis catalytic materials to generate lower molecular weight compounds. For instance, U.S. Pat. Nos. 6,841,085, 6,677,385 and 6,479,713 to Werpy et al., disclose methods for the hydrogenolysis of both carbon-oxygen and carbon-carbon bonds using a rhenium (Re)-containing multimetallic catalyst to produce products, such as propylene glycol (PG). The Re-containing catalyst may also include Ni, Pd, Ru, Co, Ag, Au, Rh, Pt, Ir, Os and Cu. The conversion takes place at temperatures in a range from 140° C. to 250° C., and more preferably 170° C. to 220° C., and a hydrogen pressure between 600 psi to 1600 psi hydrogen.

Dasari et al. also disclose hydrogenolysis of glycerol to PG in the presence of hydrogen from an external source, at temperatures in a range from 150° C. to 260° C. and a hydrogen pressure of 200 psi, over nickel, palladium, platinum, copper and copper-chromite catalysts. The authors reported increased yields of propylene glycol with decreasing water concentrations, and decreasing PG selectivity at temperatures above 200° C. and hydrogen pressures of 200 psi. The authors further reported that nickel, ruthenium and palladium were not very effective for hydrogenating glycerol. Dasari, M. A.; Kiatsimkul, P.-P.; Sutterlin, W. R.; Suppes, G. J. *Low-pressure hydrogenolysis of glycerol to propylene glycol* Applied Catalysis, A: General, 281(1-2), p. 225 (2005).

U.S. patent application Ser. No. 11/088,603 (Pub. No. US2005/0244312 A1) to Suppes et al., disclose a process for converting glycerin into lower alcohols having boiling points less than 200° C., at high yields. The process involves the conversion of natural glycerin to propylene glycol through an acetol intermediate at temperatures from 150° C. to 250° C., at a pressure ranging from 1 to 25 bar (14.5 to 363 psi), and preferably from 5 to 8 bar (72.5 to 116 psi), over a palladium, nickel, rhodium, zinc, copper, or chromium catalyst. The reaction occurs in the presence or absence of hydrogen, with the hydrogen provided by an external source. The glycerin is reacted in solution containing 50% or less by weight water, and preferably only 5% to 15% water by weight.

Regardless of the above, there remains a need for more cost-effective catalysts and methods for reacting complex and higher concentrations of carbohydrate feedstocks to the desired lower molecular weight compounds, such alcohols, ketones, aldehydes, carboxylic acids and other polyols. To be cost effective, the catalysts employed must provide effective conversion to the desired compounds at higher yields and without significant impact by the presence of water and undesired reaction products, such as CO and CO2.

SUMMARY

The present invention is directed to catalysts and methods for converting oxygenated hydrocarbons to lower molecular weight oxygenated compounds using a heterogeneous catalyst containing platinum, ruthenium and tin. In one aspect, the method includes reacting an aqueous feedstock solution with hydrogen, at a temperature of between 100° C. and 300° C., in the presence of a heterogeneous hydrodeoxygenation (HDO) catalyst, to produce a reaction product containing one or more oxygenated compounds selected from the group consisting of a polyol, a ketone, an aldehyde, a carboxylic acid and an alcohol. The aqueous feedstock solution comprises water and one or more water soluble oxygenated hydrocarbons selected from the group consisting of a starch, a polysaccharide, a disaccharide, a monosaccharide, a polyhydric alcohol, a sugar, a sugar alcohol, and combinations thereof. The heterogeneous HDO catalyst is a solid catalyst containing ruthenium, platinum and tin.

In one aspect of the invention, the HDO catalyst contains at least 0.1 wt % platinum, at least 0.1 wt % ruthenium, and at least 0.1 wt % tin. In another aspect, the HDO catalyst contains less than 6.0 wt % platinum, or less than 6.0 wt % ruthenium, or less than 6.0 wt % tin. In yet another aspect, the HDO catalyst further comprises a support selected from the group consisting of carbon, silica, silica-alumina, alumina, iron aluminate, zirconia, tungsten, titania, ceria, magnesium vanadia, nitride, boron nitride, heteropolyacids, hydroxyapatite, zinc oxide, chromia, oxides of the foregoing, and mixtures thereof.

The hydrogen used in the current invention may be provided by an external source, derived in situ, or both. In one embodiment, the hydrogen is generated in situ by catalytically reacting a portion of the aqueous feedstock solution, at a temperature of between 80° C. and 400° C., in the presence of an aqueous phase reforming (APR) catalyst comprising one or more Group VIII metals. In a second embodiment, the hydrogen is generated in situ by catalytically reacting a second aqueous feedstock solution comprising water and a second water-soluble oxygenated hydrocarbon having two or more carbon atoms, at a temperature of between 80° C. and 400° C., in the presence of an APR catalyst comprising one or more Group VIII metals. The Group VIII metals may be used alone or in combination with other active metals or supports. In this aspect, the Group VIII metal may be alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

In certain embodiments, the hydrogen is provided directly as part of a gaseous mixture containing carbon monoxide or carbon dioxide. In one such embodiment, the gaseous mixture is generated by catalytically reacting a portion of the aqueous feedstock solution, at a temperature of between 80° C. and 400° C., in the presence of an APR catalyst comprising one or more Group VIII metals. In another embodiment, the gaseous mixture is generated by catalytically reacting a second aqueous feedstock solution comprising water and a second water-soluble oxygenated hydrocarbon having two or more carbon atoms, at a temperature of between 80° C. and 400° C., in the presence of an APR catalyst comprising one or more Group VIII metals. The Group VIII metals may be used alone or alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

The oxygenated hydrocarbons are generally carbohydrates derived from biomass. The water soluble oxygenated hydrocarbon can be a sugar or sugar alcohol selected from the group consisting of glucose, fructose, sucrose, maltose, lactose, mannose, xylose, arabitol, erythritol, glycerol, isomalt, lactitol, malitol, mannitol, sorbitol, xylitol, and alditol. The aqueous feedstock solution can comprise at least 20 wt % glycerol.

The reaction products include oxygenated compounds having a lower molecular weight than the oxygenated hydrocarbons from which they are derived. The method can produce a polyol, a ketone, an aldehyde, a carboxylic acid, a diol, an alcohol, or combinations thereof. The reaction product can produce propylene glycol and ethylene glycol. The method can also produce propylene glycol at a yield of 40% or greater. The method may also produce propylene glycol in combination with one or more of the following products: a second diol, a carboxylic acid, an aldehyde, and an alcohol.

In another aspect of the invention, a method is provided for generating propylene glycol. The method includes the step of contacting a heterogeneous catalyst comprising platinum, ruthenium, and tin, with hydrogen and an aqueous feedstock solution comprising water and glycerol, at (i) a temperature of about 200° C. to 280° C.; (ii) a weight hourly space velocity of at least about 0.1 gram of glycerol per gram of the heterogeneous catalyst per hour; and (iii) a pressure where the water and the glycerol remain condensed liquids or a pressure where the water and the glycerol are in the vapor phase. In one embodiment, the heterogeneous catalyst contains between 2.0 wt % and 6.0 wt % platinum, 2.0 wt % and 6.0 wt % ruthenium, 2.0 wt % and 6.0 wt % tin, on a zirconia support. In another embodiment, the feedstock comprises at least about 20 wt % glycerol. In yet another embodiment, the feedstock is contacted with the heterogeneous catalyst at a weight hourly space velocity of about 0.1 to 10.0 grams of glycerol per gram of the heterogeneous catalyst per hour and a pressure of about 625-700 psig. In still yet another embodiment, the reaction product has a carbon yield of propylene glycol of 40% or greater.

The propylene glycol may be produced using hydrogen provided by an external source, derived in situ, or both. When derived in situ, the hydrogen is generated by catalytically reacting a portion of the water and glycerol in the presence of an aqueous phase reforming catalyst comprising one or more Group VIII metals, at a temperature of between 80° C. and 400° C. and a pressure where the water and glycerol are condensed liquids or in the vapor phase. The Group VIII metal may be alone or alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

The present invention is also directed to a composition of matter comprising water, hydrogen, a sugar or sugar alcohol, propylene glycol, and a catalyst composition comprising platinum, ruthenium and tin. The sugar or sugar alcohol may include, without limitation, glucose, fructose, sucrose, maltose, lactose, mannose, xylose, arabitol, erythritol, glycerol, isomalt, lactitol, malitol, mannitol, sorbitol, xylitol, and alditol.

DETAILED DESCRIPTION

The present invention relates to methods for producing polyols, ketones, carboxylic acids, aldehydes, and alcohols from biomass-derived oxygenated hydrocarbons, such sugars, sugar alcohols, saccharides and other carbohydrates, using catalysts containing platinum, ruthenium and tin. The oxygenated compounds produced are useful as industrial chemicals or chemical intermediates for liquid fuels production.

Figure 1A:
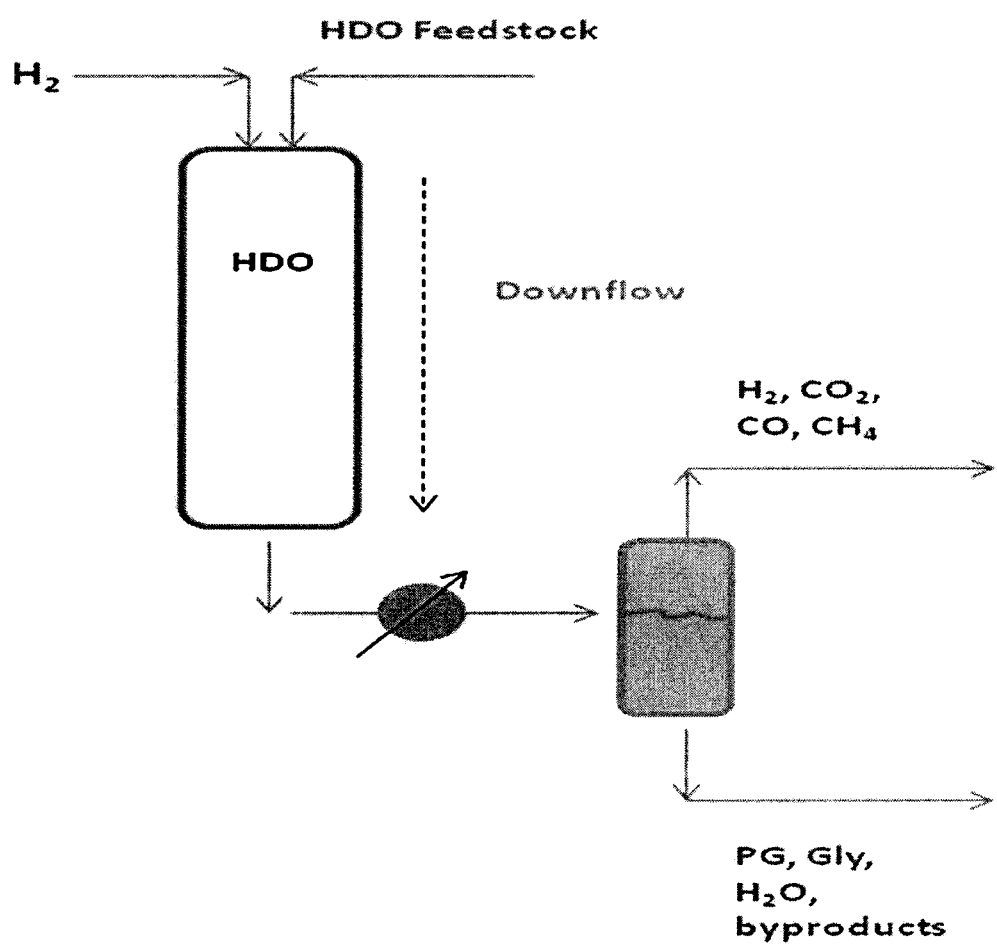
FIG. 1 is a general illustration of the claimed invention with the use of external hydrogen (FIG. 1a) or hydrogen derived in situ using aqueous phase reforming (FIG. 1b)
Figure 1B:
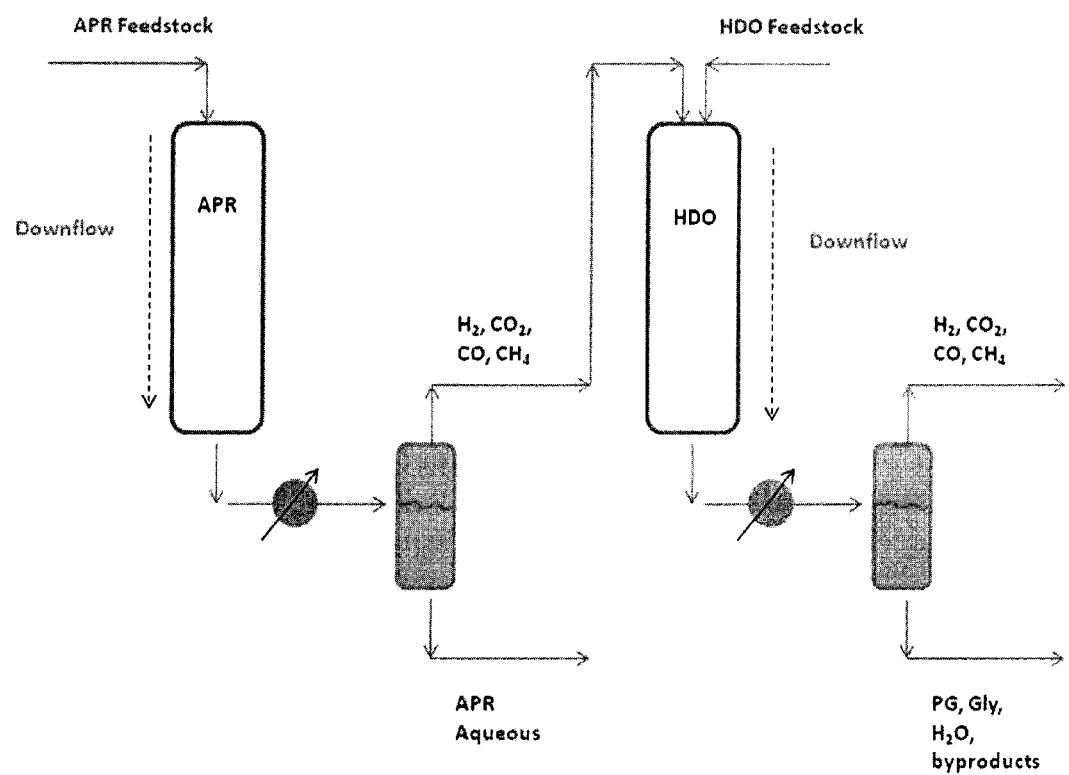

The general process is illustrated in FIG. 1. A feedstock solution containing a water-soluble oxygenated hydrocarbon is reacted with hydrogen over a heterogeneous hydrodeoxygenation (HDO) catalyst to produce oxygenated compounds having a lower molecular weight than the originating oxygenated hydrocarbons. The hydrogen may originate from any source, whether external (FIG. 1a) or derived in situ from biomass using aqueous phase reforming (FIG. 1b). The hydrogen and oxygenated hydrocarbons may also be supplemented with recycled hydrogen and oxygenated hydrocarbons derived from the process. The oxygenated hydrocarbon may be a monosaccharide, disaccharide, polysaccharide, sugar, sugar alcohol or other polyhydric alcohol.

One unique aspect about the present invention is that the oxygenated compounds are derived from biomass components using catalytic processes instead of microorganisms, enzymes, high temperature gasification or transesterification methods. The present invention can also generate hydrogen in situ to avoid reliance on external hydrogen sources, such as hydrogen generated from the steam reforming of natural gas, or the electrolysis or thermolysis of water. When in situ hydrogen is employed, the described platinum-ruthenium-tin catalyst combinations are able to unexpectedly function without any significant impact from the presence of carbon dioxide or carbon monoxide arising from the aqueous phase reforming reactions, thereby avoiding any hydrogen purification or separation requirements. When directed to the production of propylene glycol, the described catalysts also provide enhanced yields of propylene glycol as compared to other catalysts without the three combined metals as described below.

Feedstocks

Feedstocks useful in the present invention may originate from any source, but are preferably derived from biomass. As used herein, the term "biomass" refers to, without limitation, organic materials produced by plants (such as leaves, roots, seeds and stalks), and microbial and animal metabolic wastes. Common sources of biomass include: (1) agricultural wastes, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; and (4) energy crops, such as poplars, willows, switch grass, alfalfa, prairie bluestream, corn, sugarcane, sugar beets, and the like. The term also refers to the primary building blocks of the above, namely, saccharides, cellulosics, hemicellulose and starches, among others.

The feedstocks may be pure materials, purified mixtures or raw materials such as sugars and starches derived from the processing of corn, sugarcane, beet sugars, rice, wheat, or energy crops. Some applicable feedstocks are also commercially available and may be obtained as by-products from other processes, such as glycerol from biodiesel fuel production. The feedstocks can also be intermediates formed as part of a larger process or in the same process, such as sugar alcohols produced in the initial stage of sugar hydrogenation.

In general, the feedstock includes any water-soluble oxygenated hydrocarbon having three or more carbon atoms and an oxygen-to-carbon ratio of 1:1. In one aspect, the oxygenated hydrocarbon has 3 to 12 carbon atoms or 3 to 6 carbon atoms. Non-limiting examples of preferred water-soluble oxygenated hydrocarbons include monosaccharides, disaccharides, polysaccharides, sugars, sugar alcohols, alditols, hemicelluloses, cellulosic derivatives, lignocellulosic derivatives, starches, polyols and the like. Preferably, the oxygenated hydrocarbon includes sugar, sugar alcohols, saccharides and other polyhydric alcohols. More preferably, the oxygenated hydrocarbon is a sugar, such as glucose, fructose, sucrose, maltose, lactose, mannose or xylose, or a sugar alcohol, such as arabitol, erythritol, glycerol, isomalt, lactitol, malitol, mannitol, sorbitol, xylitol, arabitol, or glycol.

The water-soluble oxygenated hydrocarbons may also include alcohols derived by the hydrogenation of the foregoing. In particular, it may be preferable to convert the starting oxygenated hydrocarbon to another form that is more readily convertible to the desired oxygenated compound. Various processes are known for hydrogenating sugars to their corresponding alcohol form, including those disclosed by: B. S. Kwak et al. (WO2006/093364A1 and WO 2005/021475A1), involving the preparation of sugar alditols from monosaccharides by hydrogenation over a ruthenium catalyst; and Elliot et al. (U.S. Pat. Nos. 6,253,797 and 6,570,043), disclosing the use of a nickel and rhenium free ruthenium catalyst on a more than 75% rutile titania support to convert sugars to sugar alcohols, all incorporated herein by reference. Other suitable ruthenium catalysts are described by Arndt et al. in published U.S. patent application 2006/0009661 (filed Dec. 3, 2003), and Arena in U.S. Pat. No. 4,380,679 (filed Apr. 12, 1982), U.S. Pat. No. 4,380,680 (filed May 21, 1982), U.S. Pat. No. 4,503,274 (filed Aug. 8, 1983), U.S. Pat. No. 4,382,150 (filed Jan. 19, 1982), and U.S. Pat. No. 4,487,980 (filed Apr. 29, 1983), all incorporated herein by reference.

In other embodiments, it may also be desirable to convert the starting oxygenated hydrocarbon, such as a starch, polysaccharide, sugar, sugar alcohol or other polyhydric alcohol, to a smaller molecule that can be more readily converted to the desired oxygenates, such as by hydrogenolysis. Such smaller molecules may include polyhydric alcohols having less carbon atoms than the originating oxygenated hydrocarbon. Various processes are known for such hydrogenolysis reactions, including those disclosed by: Werpy et al. in U.S. Pat. No. 6,479,713 (filed Oct. 23, 2001), U.S. Pat. No. 6,677,385 (filed Aug. 6, 2002), U.S. Pat. No. 6,6841,085 (filed Oct. 23, 2001) and U.S. Pat. No. 7,083,094 (filed Sep. 30, 2003), all incorporated herein by reference and describing the hydrogenolysis of 5 and 6 carbon sugars and sugar alcohols to propylene glycol, ethylene glycol and glycerol using a rhenium-containing multi-metallic catalyst. Other systems include those described by Arena in U.S. Pat. No. 4,401,823 (filed May 18, 1981) directed to the use of a carbonaceous pyropolymer catalyst containing transition metals (such as chromium, molybdenum, tungsten, rhenium, manganese, copper, cadmium) or Group VIII metals (such as iron, cobalt, nickel, platinum, palladium, rhodium, ruthenium, iridium and osmium) to produce alcohols, acids, ketones, and ethers from polyhydroxylated compounds, such as sugars and sugar alcohols, and U.S. Pat. No. 4,496,780 (filed Jun. 22, 1983) directed to the use of a catalyst system having a Group VIII noble metal on a solid support with an alkaline earth metal oxide to produce glycerol, ethylene glycol and 1,2-propanediol from carbohydrates, each incorporated herein by reference. Another system includes that described by Dubeck et al. in U.S. Pat. No. 4,476,331 (filed Sep. 6, 1983) directed to the use of a sulfide-modified ruthenium catalyst to produce ethylene glycol and propylene glycol from larger polyhydric alcohols, such as sorbitol, also incorporated herein by reference. Other systems include those described by Saxena et al., "Effect of Catalyst Constituents on (Ni, Mo and Cu)/Kieselguhr-Catalyzed Sucrose Hydrogenolysis," Ind. Eng. Chem. Res. 44, 1466-1473 (2005), describing the use of Ni, W, and Cu on a Kieselguhr support, incorporated herein by reference.

Production of Oxygenated Compounds

The oxygenated compounds are prepared by reacting an aqueous feedstock solution containing water and the water soluble oxygenated hydrocarbons with hydrogen over an HDO catalyst containing platinum, ruthenium and tin. The hydrogen utilized may be hydrogen generated in situ using aqueous phase reforming (in situ generated hydrogen or APR hydrogen), or a combination of APR hydrogen, external hydrogen or recycled hydrogen, or just simply external hydrogen or recycled hydrogen. The term "external hydrogen" refers to hydrogen that does not originate from the feedstock solution, but is added to the reactor system from an external source. The term "recycled hydrogen" refers to unconsumed hydrogen that originates from the feedstock solution, and which is collected and then recycled back into the reactor system for further use. External hydrogen and recycled hydrogen may also be referred to collectively or individually as "supplemental hydrogen." In general, supplemental hydrogen may be added for purposes of supplementing the APR hydrogen, or to substitute the inclusion of an APR hydrogen production step, or to increase the reaction pressure within the system, or to increase the molar ratio of hydrogen to carbon and/or oxygen in order to enhance the production yield of certain reaction product types, such as ketones and alcohols.

In processes utilizing APR hydrogen, the oxygenate compounds are prepared by catalytically reacting a portion of the aqueous feedstock solution containing water and the water soluble oxygenated hydrocarbons in the presence of an APR catalyst at a reforming temperature and reforming pressure to produce the APR hydrogen, and catalytically reacting the APR hydrogen (and recycled hydrogen and/or external hydrogen, as applicable) with a portion of the feedstock solution in the presence of a Pt:Ru:Sn HDO catalyst at a temperature and pressure to produce the desired oxygenate compounds. In systems utilizing recycled hydrogen or external hydrogen as a hydrogen source, the oxygenate compounds are simply prepared by catalytically reacting the recycled hydrogen and/or external hydrogen with the feedstock solution in the presence of the Pt:Ru:Sn HDO catalyst.

The Pt:Ru:Sn HDO catalyst is a heterogeneous catalyst containing a combination of platinum, ruthenium and tin, whether alloyed or admixed in combination. Loading of the platinum is in the range of 0.1 wt % to 6 wt %, with weight percentages of 0.10% and 0.05% increments between, such as 1.00%, 1.10%, 1.15%, 2.00%, 2.50%, 5.00%, etc. Loading of the ruthenium is in the range of 0.1 wt % to 6 wt %, with weight percentages of 0.10% and 0.05% increments between, such as 1.00%, 1.10%, 1.15%, 2.00%, 2.50%, 5.00%, etc. Loading of the tin is in the range of 0.1 wt % to 6 wt %, with weight percentages of 0.10% and 0.05% increments between, such as 1.00%, 1.10%, 1.15%, 2.00%, 2.50%, 5.00%, etc.

The preferred atomic ratio of the platinum to ruthenium is in the range of 0.25-to-1 to 10-to-1, including any ratios between, such as 0.50, 1.00, 2.50, 5.00, and 7.50-to-1. The preferred atomic ratio of the tin to ruthenium is in the range of 0.25-to-1 to 10-to-1, including any ratios between, such as 0.50, 1.00, 2.50, 5.00, and 7.50-to-1. The preferred atomic ratio of the platinum to tin is in the range of 0.25-to-1 to 10-to-1, including any ratios between, such as 0.50, 1.00, 2.50, 5.00, and 7.50-to-1. If the catalyst is adhered to a support, the combination of the catalyst materials is from 0.30 wt % to 18 wt % of the support.

In various embodiments above, the catalyst system includes a support suitable for suspending the HDO catalyst in the feedstock solution. The support should be one that provides a stable platform for the HDO catalyst and reaction conditions. The support may take any form which is stable at the chosen reaction conditions to function at the desired levels, and specifically stable in aqueous feedstock solutions. Such supports include, without limitation, carbon, silica, silica-alumina, alumina, iron aluminate, zirconia, tungsten, titania, ceria, vanadia, nitride, boron nitride, heteropolyacids, hydroxyapatite, zinc oxide, chromia, oxides of the foregoing, and mixtures thereof. Nanoporous supports such as zeolites, carbon nanotubes, or carbon fullerene may also be used.

One catalyst support is zirconia. The zirconia may be produced via precipitation of zirconium hydroxide from zirconium salts, through sol-gel processing, or any other method. The zirconia is preferably present in a crystalline form achieved through calcination of the precursor material at temperatures exceeding 400° C. and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y. In one embodiment, the catalyst includes Pt, Ru and Sn on monoclinic zirconia.

Another catalyst support is tungstated zirconia. The tungstated zirconia may be produced via impregnation of zirconium hydroxide with an aqueous solution containing a tungsten salt, precipitation from zirconium and tungsten salts through sol-gel processing, or any other method. The tungstated zirconia is preferably present in a mixed oxide crystalline form achieved through calcination of the precursor material at temperatures exceeding 400° C., preferentially above 600° C., and may include both tetragonal and monoclinic crystalline zirconia phases as well as polytungsten oxide clusters present on the catalyst support surface. A modifying agent may be added to improve the textural or catalytic properties of the tungstated zirconia. Such modifying agents include, without limitation, sulfate, phosphate, titania, silica, and oxides of Group IIIB metals, especially Ce, La, or Y. In one embodiment, the catalyst includes Pt, Ru and Sn on tungstated zirconia.

Another catalyst support is carbon, especially carbon supports having relatively high surface areas (greater than about 100 square meters per gram). Such carbons include activated carbon (granulated, powdered, or pelletized), activated carbon cloth, felts, or fibers, carbon nanotubes or nanohorns, carbon fullerene, high surface area carbon honeycombs, carbon foams (reticulated carbon foams), and carbon blocks. The carbon may be produced via either chemical or steam activation of peat, wood, lignite, coal, coconut shells, olive pits, and oil based carbon. Another support is granulated activated carbon produced from coconuts.

Yet another catalyst support is titania. The titania may be produced via precipitation from titanium salts, through sol-gel processing, or any other method. The titania is preferably present in a crystalline form and may include both anatase and rutile crystalline phases. A modifying agent may be added to improve the textural or catalytic properties of the titania. Such modifying agents include, without limitation, sulfate, silica, tungstenate, and oxides of Group IIIB metals, especially Ce, La, or Y.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungsten, silanes, lanthanides, alkali compounds or alkali earth compounds. For carbon supports, the carbon may be pretreated with steam, oxygen (from air), inorganic acids or hydrogen peroxide to provide more surface oxygen sites. The pretreated carbon may also be modified by the addition of oxides of Group IVB and Group VB. It is preferred to use oxides of Ti, V, Zr and mixtures thereof.

Conventional methods for preparing catalyst systems are well known in the art. Common methods include incipient wetting, evaporative impregnation, chemical vapor deposition, wash-coating, magnetron sputtering techniques, and the like. The method chosen to fabricate the HDO catalyst is not critical to the function of the invention, with the proviso that different catalysts will yield different results, depending upon considerations such as overall surface area, porosity, etc.

To produce the oxygenated compounds, the oxygenated hydrocarbon is combined with water to provide an aqueous feedstock solution having a concentration effective for causing the formation of the desired reaction products. The water-to-carbon ratio on a molar basis is preferably from about 0.5:1 to about 100:1, including ratios such as 1:1, 2:1, 3:1, 4:1, 5:1, 6:1, 7:1, 8:1, 9:1, 10:1, 15:1, 25:1, 50:1, 75:1, 100:1, and any ratios there-between. The feedstock solution may also be characterized as a solution having at least 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included.

The feedstock solution is reacted with hydrogen in the presence of the Pt:Ru:Sn HDO catalyst at temperature and pressure conditions, and weight hourly space velocity, effective to produce the desired oxygenated compounds. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the HDO catalyst over time, will limit the extent of the reactions which may occur, thereby causing increased yield for higher level diols and triols, with a reduction in ketone and alcohol yields.

The reaction temperature and pressures are preferably selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In condensed phase liquid reactions, the pressure within the reactor must be sufficient to maintain the reactants in the condensed liquid phase at the reactor inlet. For liquid phase reactions, the reaction temperature may be from about 100° C. to 300° C., and the reaction pressure from about 72 psig to 1300 psig. In one embodiment, the reaction temperature is between about 120° C. and 300° C., or between about 200° C. and 280° C., or between about 220° C. and 240° C., and the reaction pressure is between about 145 and 1200 psig, or between about 200 and 725 psig, or between about 365 and 700 psig, or between about 625 and 700 psig.

For vapor phase reactions, the reaction should be carried out at a temperature where the vapor pressure of the oxygenated hydrocarbon is at least about 0.1 atm (and preferably a good deal higher), and the thermodynamics of the reaction are favorable. This temperature will vary depending upon the specific oxygenated hydrocarbon compound used, but is generally in the range of from about 100° C. to 600° C. for vapor phase reactions. Preferably, the reaction temperature is between about 120° C. and about 300° C., or between about 200° C. and about 280° C., or between about 220° C. and about 260° C.

In general, the reaction should be conducted under conditions where the residence time of the feedstock solution over the catalyst is appropriate to generate the desired products. For example, the WHSV for the reaction may be at least about 0.1 gram of oxygenated hydrocarbon per gram of catalyst per hour, and more preferably the WHSV is about 0.1 to 40.0 g/g hr, including a WHSV of about 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr.

The hydrogen used in the reaction is preferably in-situ generated hydrogen, but may also be external or recycled hydrogen. The amount (moles) of external hydrogen introduced to the feedstock may be between 0-100%, 0-95%, 0-90%, 0-85%, 0-80%, 0-75%, 0-70%, 0-65%, 0-60%, 0-55%, 0-50%, 0-45%, 0-40%, 0-35%, 0-30%, 0-25%, 0-20%, 0-15%, 0-10%, 0-5%, 0-2%, or 0-1% of the total number of moles of the oxygenated hydrocarbon(s) in the feedstock, including all intervals between. When the feedstock solution, or any portion thereof, is reacted with APR hydrogen and external hydrogen, the molar ratio of APR hydrogen to external hydrogen is at least 1:100, 1:50, 1:20; 1:15, 1:10, 1:5; 1:3, 1:2, 1:1, 2:1, 3:1, 5:1, 10:1, 15:1, 20:1, 50:1, 100:1, and ratios between (including 4:1, 6:1, 7:1, 8:1, 9:1, 11:1, 12:1, 13:1, 14:1, 15:1, 16:1, 17:1, 18:1 and 19:1, and vice-versa). In one embodiment, the oxygenated hydrocarbon is reacted with hydrogen in the presence of external hydrogen.

In-Situ Hydrogen Production

One unique aspect of the present invention is the ability of the Pt:Ru:Sn HDO catalyst to effectively convert oxygenated hydrocarbons to the desired oxygenated compounds utilizing in situ generated APR hydrogen, without the anticipated negative effects arising from the presence of carbon monoxide and/or carbon dioxide derived from the APR process.

The APR hydrogen is produced from the feedstock under aqueous phase reforming conditions using an aqueous phase reforming catalyst (APR catalyst). The APR catalyst is preferably a heterogeneous catalyst capable of catalyzing the reaction of water and oxygenated hydrocarbons to form hydrogen under the conditions described below. In one embodiment, the APR catalyst includes a support and at least one Group VIIIB metal, Fe, Ru, Os, Ir, Co, Rh, Pt, Pd, Ni, alloys and combinations thereof. The APR catalyst may also include at least one additional material from Group VIIIB, Group VIIB, Group VIB, Group VB, Group IVB, Group IIB, Group IB, Group IVA, Group VA metals and lanthanoids, such as Cu, B, Mn, Re, Cr, Mo, Bi, W, V, Nb, Ta, Ti, Zr, Y, La, Sc, Zn, Cd, Ag, Au, Sn, Ge, P, Al, Ga, In, Ti, Ce, alloys and combinations thereof. The preferred Group VIIB metal includes Re, Mn, or combinations thereof. The preferred Group VIB metal includes Cr, Mo, W, or a combination thereof. The preferred Group VIIIB metals include Pt, Rh, Ru, Pd, Ni, or combinations thereof. The supports may include any one of the catalyst supports described for the HDO catalyst above, depending on the desired activity of the catalyst system. The APR catalyst may also be atomically identical to the HDO catalyst.

Preferred loading of the primary Group VIIIB metal is in the range of 0.25 wt % to 25 wt % on carbon, with weight percentages of 0.10% and 0.05% increments between, such as 1.00%, 1.10%, 1.15%, 2.00%, 2.50%, 5.00%, 10.00%, 12.50%, 15.00% and 20.00%. The preferred atomic ratio of the second material is in the range of 0.25-to-1 to 10-to-1, including ratios between, such as 0.50, 1.00, 2.50, 5.00, and 7.50-to-1.

The APR catalyst may also be formulated to include oxides of Group IIIB, and associated rare earth oxides. In such event, the preferred components would be oxides of either lanthanum or cerium. The preferred atomic ratio of the Group IIIB compounds to the primary Group VIIIB metal is in the range of 0.25-to-1 to 10-to-1, including ratios between, such as 0.50, 1.00, 2.50, 5.00, and 7.50-to-1.

Another APR catalyst composition is one containing platinum and rhenium. The preferred atomic ratio of Pt to Re is in the range of 0.25-to-1 to 10-to-1, including ratios there-between, such as 0.50, 1.00, 2.50, 5.00, and 7.00-to-1. The preferred loading of the Pt is in the range of 0.25 wt % to 5.0 wt %, with weight percentages of 0.10% and 0.05% between, such as 0.35%, 0.45%, 0.75%, 1.10%, 1.15%, 2.00%, 2.50%, 3.0%, and 4.0%.

The temperature and pressure conditions for in situ hydrogen generation are preferably selected to maintain at least a portion of the feedstock in the liquid phase at the reactor inlet. The reforming temperature and pressure conditions may also be selected to more favorably produce the desired products in the vapor-phase. In general, the APR reaction should be conducted at a temperature where the thermodynamics are favorable. For instance, the minimum pressure required to maintain a portion of the feedstock in the liquid phase will vary with the reaction temperature. As temperatures increase, higher pressures will generally be required to maintain the feedstock in the liquid phase. Any pressure above that required to maintain the feedstock in the liquid phase (i.e., vapor-phase) is also a suitable operating pressure. For vapor phase reactions, the reaction should be conducted at a reforming temperature where the vapor pressure of the oxygenated hydrocarbon compound is at least about 0.1 atm (and preferably a good deal higher), and the thermodynamics of the reaction are favorable. The temperature will vary depending upon the specific oxygenated hydrocarbon compound used, but is generally in the range of from about 100° C. to 450° C., or from about 100° C. to 300° C., for reactions taking place in the vapor phase. For liquid phase reactions, the reaction temperature may be from about 80° C. to 400° C., and the reaction pressure from about 72 psig to 1300 psig.

In one embodiment, the reaction temperature is between about 100° C. and 400° C., or between about 120° C. and 300° C., or between about 200° C. and 280° C., or between about 150° C. and 270° C. The reaction pressure is preferably between about 72 and 1300 psig, or between about 72 and 1200 psig, or between about 145 and 1200 psig, or between about 200 and 725 psig, or between about 365 and 700 psig, or between about 600 and 650 psig.

A condensed liquid phase method may also be performed using a modifier that increases the activity and/or stability of the APR catalyst system. It is preferred that the water and the oxygenated hydrocarbon are reacted at a suitable pH of from about 1.0 to 10.0, or at a pH of from about 4.0 to 10.0, including pH value increments of 0.1 and 0.05 between. Generally, the modifier is added to the feedstock solution in an amount ranging from about 0.1% to about 10% by weight as compared to the total weight of the catalyst system used, although amounts outside this range are included within the present invention.

Alkali or alkali earth salts may also be added to the feedstock solution to optimize the proportion of hydrogen in the reaction products. Examples of suitable water-soluble salts include one or more selected from the group consisting of an alkali or an alkali earth metal hydroxide, carbonate, nitrate, or chloride salt. For example, adding alkali (basic) salts to provide a pH of about pH 4.0 to about pH 10.0 can improve hydrogen selectivity of reforming reactions.

The addition of water-soluble acidic compounds may also provide increased selectivity to the desired reaction products. The water-soluble acid may include nitrate, phosphate, sulfate, chloride salts, and mixtures thereof. If an acidic modifier is used, it is preferred that it be present in an amount sufficient to lower the pH of the aqueous feed stream to a value between about pH 1.0 and about pH 4.0. Lowering the pH of a feed stream in this manner may increase the proportion of oxygenates in the final reaction products.

In general, the reaction should be conducted under conditions where the residence time of the feedstock solution over the APR catalyst is appropriate to generate an amount of APR hydrogen sufficient to react with a second portion of the feedstock solution over the HDO catalyst to provide the desired oxygenated compounds. For example, the WHSV for the reaction may be at least about 0.1 gram of oxygenated hydrocarbon per gram of APR catalyst, and preferably between about 1.0 to 40.0 grams of oxygenated hydrocarbon per gram of APR catalyst, and more preferably between about 0.5 to 8.0 grams of oxygenated hydrocarbon per gram of APR catalyst. In terms of scaled-up production, after start-up, the APR reactor system should be process controlled so that the reactions proceed at steady-state equilibrium.

Reactor System

The reactions described herein may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. Preferably, the present invention is practiced utilizing a continuous-flow system at steady-state equilibrium.

Figure 2:
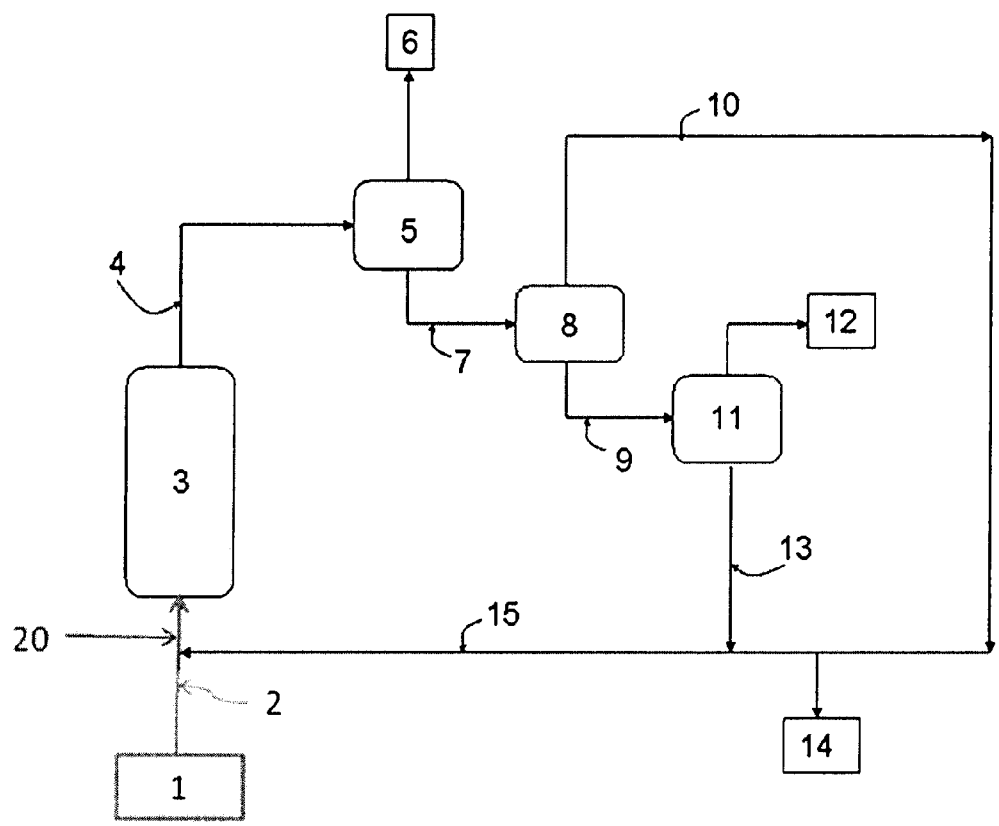
FIG. 2 is a schematic diagram illustrating a process for converting an aqueous feedstock solution in accordance with the present invention using external hydrogen.

FIG. 2 is a schematic illustration showing one process for converting a feedstock solution 1 to a final desired product 12 using a single reactor 3 containing a Pt:Ru:Sn HDO catalyst. The feedstock solution 1 includes water combined with one or more oxygenated hydrocarbons, such as glycerol, sugar or sugar alcohol. The stream 2 is fed via an HPLC pump (not shown) to reactor system 3 having the Pt:Ru:Sn HDO catalyst, where it subsequently reacts with hydrogen provided by stream 20 to generate the desired products.

The effluent stream 4 from the reactor 3 contains a mixture of water, hydrogen, carbon dioxide, light hydrocarbons, polyols, alcohols, ketones, acids, aldehydes and unreacted feedstock. The mixture is cooled and separated in a two-phase separator 5, where the non-condensed gases (such as hydrogen, carbon dioxide, methane, ethane and propane) are removed via stream 6 from the phase containing the water soluble products and unreacted feedstock. The non-condensable stream 6 can be either combusted to create process heat (i.e., heat for driving the reaction in reactor 3) or sent to a separation system where hydrogen can be recovered for recycle back to stream 20. The aqueous stream 7 may be sent to a separator 8 where the light alcohols (methanol and ethanol) and water are removed and recycled back via stream 10 to the reactor inlet. A purge stream 14 is included to prevent a build-up of water in the reactor system.

A crude product stream 9, containing unreacted feedstock and the desired polyols, ketones, aldehydes, carboxylic acids and/or alcohol products, is recovered from separator 8 via stream 9 and sent to a finishing separator where the desired product 12 is separated from unreacted feedstock 13. The unreacted feedstock stream is then added to stream 10 and recycled back to the reactor system via stream 15.

In systems producing both hydrogen and oxygenated compounds, the reactor system includes at least a reforming bed adapted to receive an aqueous feedstock solution to produce hydrogen, and a HDO bed adapted to receive the hydrogen and an aqueous solution to produce the desired oxygenated compounds. The HDO bed may be positioned within the same reactor vessel along with the reforming bed or in a second reactor vessel in communication with a first reactor vessel having the reforming bed.

If the APR catalyst and Pt:Ru:Sn HDO catalyst are within a single chamber, the APR catalyst and Pt:Ru:Sn HDO catalyst may be placed in a stacked configuration to allow the feedstock solution to first contact the APR catalyst and then the Pt:Ru:Sn HDO catalyst. The reaction beds for the APR catalyst and Pt:Ru:Sn HDO catalyst may also be placed side-by-side, depending on the particular flow mechanism employed. In either case, the feedstock solution may be introduced into the reaction vessel through one or more inlets, and then directed across the catalysts for processing. In another embodiment, the feedstock solution is directed across the APR catalyst to produce a gaseous mixture of APR hydrogen and carbon monoxide or carbon dioxide, with the gaseous mixture and the remaining feedstock solution then directed across the Pt:Ru:Sn HDO catalyst to produce the oxygenated compounds.

In parallel configurations, the feedstock solution may be separated to direct a first portion of the feedstock solution to the reforming bed where a gaseous mixture of APR hydrogen and carbon monoxide or carbon dioxide is produced, and a second portion to an HDO bed where the oxygenated compounds are produced using the in situ generated APR hydrogen. Alternatively, the reactor may be configured to accommodate the use of two separate feedstock solutions, with the first feedstock solution directed to the APR reactor vessel and the second feedstock solution directed to the HDO reactor vessel. In a sequential configuration, the reactor may be designed so that the feedstock solution flows through the APR reactor vessel and into the HDO reactor vessel. In either of these systems, because the APR hydrogen is produced in-situ, the pressure is provided by a pumping mechanism that also drives the feedstock solution through the reactor chambers.

Figure 3:
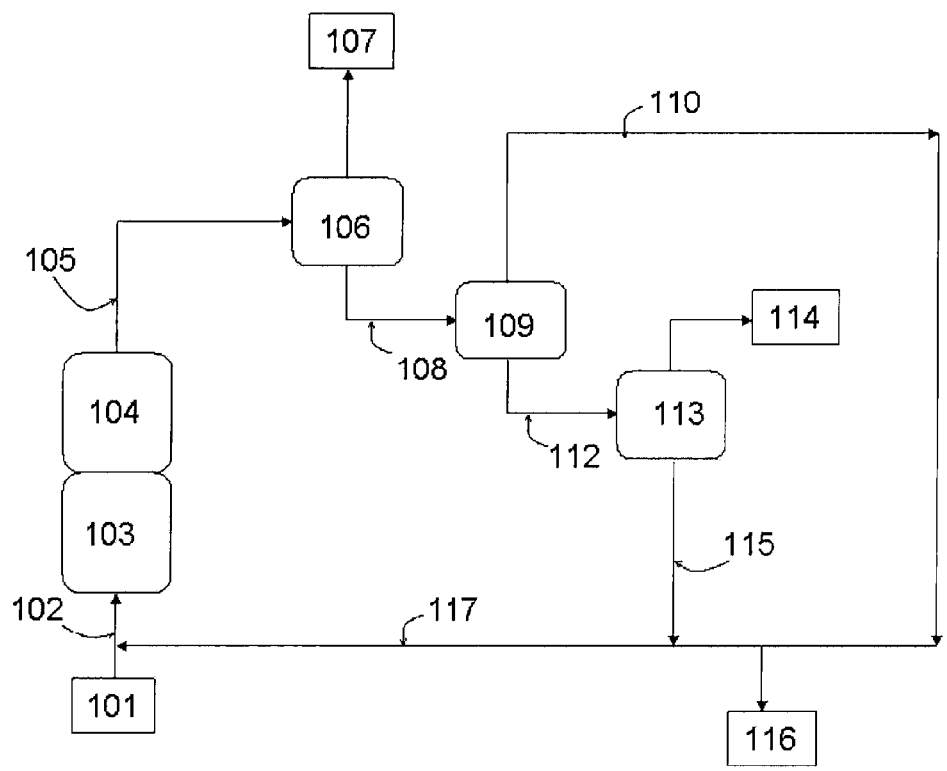
FIG. 3 is a schematic diagram illustrating a process for generating reaction products from an aqueous feedstock solution using a reactor having a first reaction chamber for generating hydrogen and a second hydrodeoxygenation chamber.

FIG. 3 is a schematic showing a process for converting a feedstock solution 101 to a final diol product 114 using a reactor system that includes a first reactor bed 103 having an APR catalyst and a second reactor bed 104 having a Pt:Ru:Sn HDO catalyst. The feedstock solution 101 includes water combined with one or more oxygenated hydrocarbons, such as sugar alcohol or glycerol. Feedstock solution 101 is combined with a recycle stream 117 containing unreacted polyols, water, and underdesirable byproducts (e.g., methanol and ethanol). The combined stream 102 is fed via an HPLC pump (not shown) to first reactor bed 103 where a portion of the stream reacts with water over the APR catalyst to form APR hydrogen. The recycled alcohols (methanol and ethanol) also react with water over the APR catalyst to form APR hydrogen and light hydrocarbons, such as methane and ethane.

Effluent containing APR hydrogen, water, carbon dioxide, carbon monoxide, light hydrocarbons and polyols move from first reactor bed 103 to second reactor bed 104 where the APR hydrogen reacts with a portion of the polyols to generate the desired products. In this illustration, the reactor bed 103 and reactor bed 104 are set in an up-flow orientation to allow the generated APR hydrogen to percolate from reactor bed 103 through second reactor bed 104 to maximize the interaction of APR hydrogen and stream 102 over the Pt:Ru:Sn HDO catalyst. Reactor beds 103 and 104 may also be designed to accommodate down-flow or horizontal-flow orientations.

The effluent stream 105 from the reactor system contains a mixture of water, hydrogen, carbon dioxide, carbon monoxide, light hydrocarbons, light alcohols (methanol and ethanol), diol and polyol products, and unreacted feedstock. The mixture is cooled and separated in a two-phase separator 106 where the non-condensable gases (such as hydrogen, carbon dioxide, carbon monoxide, methane, ethane and propane) are removed via stream 107 from the phase containing the water soluble alcohols, diols and polyols. The non-condensable stream 107 can be either combusted to create process heat or sent to a separation system where hydrogen is recovered for possible recycle back to stream 102. The aqueous stream 108 is sent to a separator 109 where the light alcohols (methanol and ethanol) and water are removed and recycled back via stream 110 to the reactor inlet. A purge stream 116 is included to prevent a build-up of water in the reactor system.

A crude product stream 112, containing unreacted feedstock and the desired polyol, diol and/or alcohol products, is recovered from separator 109 via stream 112 and sent to a finishing separator 113 where the desired product 114 is separated from unreacted feedstock 115. The unreacted feedstock stream is added to stream 110 and recycled back to the reactor system via stream 117.

The reactor system may also include additional outlets to allow for the removal of portions of the reactant stream to further advance or direct the reaction to the desired reaction products, and to allow for the collection and recycling of reaction byproducts for use in other portions of the system. The reactor system may also include additional inlets to allow for the introduction of supplemental materials to further advance or direct the reaction to the desired reaction products, and to allow for the recycling of reaction byproducts for use in other aspects of the process. For example, the system may be designed such that excess hydrogen is produced over the APR catalyst, with a portion of the excess hydrogen removed and used in other upstream processes, such as feedstock pre-treatment processes and hydrogenation or hydrogenolysis reactions.

Figure 4:
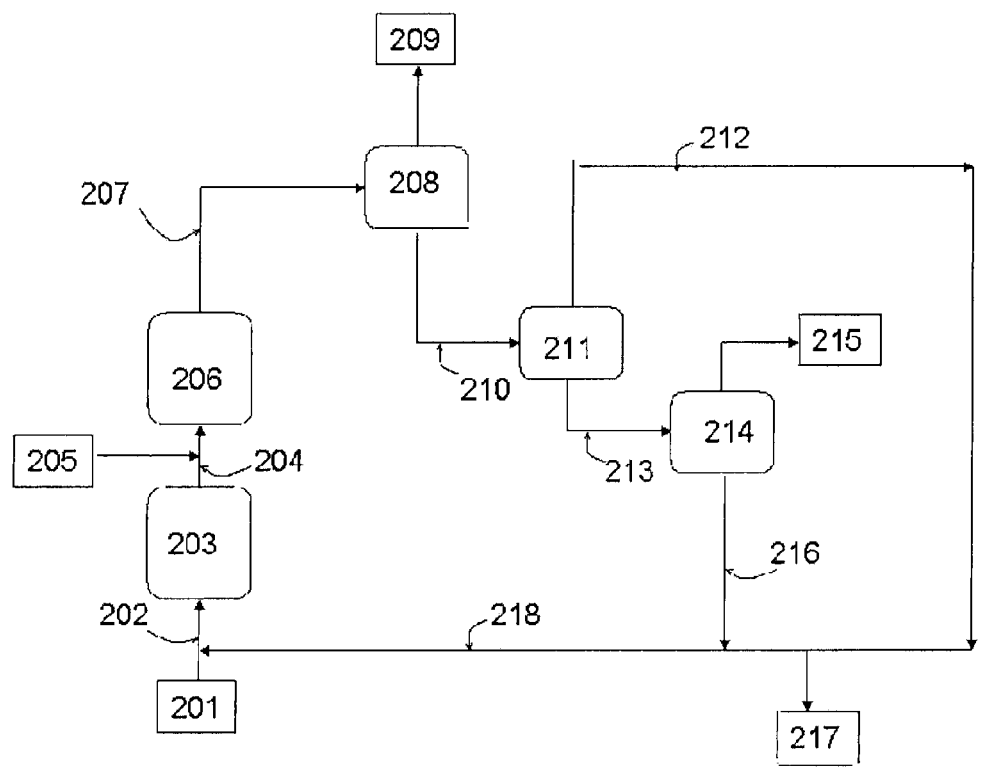
FIG. 4 is a schematic diagram illustrating a process for generating reaction products from an aqueous feedstock solution with an added supplement using a reactor having a first reaction chamber for generating hydrogen and a second hydrodeoxygenation chamber.

FIG. 4 is a schematic showing another process for converting a feedstock solution 201 to a final product 215 with the introduction of a supplement 205. Supplement 205 may include various salts, acids, additional feedstock solution, hydrogen or byproducts of the process.

Feedstock solution 201 includes water combined with one or more oxygenated hydrocarbons, such as glycerol, sugar alcohol or corn syrup. Feedstock solution 201 may contain the same combination as feedstock solution 205 or a combination of one or more low cost oxygenated compounds, such as glycerol from a biodiesel process, ethylene glycol from spent antifreeze, or low cost alcohols. Stream 201 may also be combined with recycle stream 218, which contains unreacted polyols, water and underdesirable byproducts, such as methanol and ethanol, to form combined stream 202.

Combined stream 202 is fed via an HPLC pump (not shown) to reactor bed 203 having an APR catalyst. Oxygenated hydrocarbons in combined stream 202 react with water over the APR catalyst to form APR hydrogen, while the recycled alcohols (i.e., methanol and ethanol) form hydrogen and light hydrocarbons, such as methane and ethane.

Effluent from first reactor bed 204, containing APR hydrogen, water, carbon dioxide, carbon monoxide, light hydrocarbons, and unreacted hydrocarbons, is combined with supplement 205. In this illustration, supplement 205 is a feedstock solution containing a higher grade of oxygenated hydrocarbons. The combined effluent 204 and supplement 205 are directed to reactor bed 206 that includes a Pt:Ru:Sn HDO catalyst for reacting the APR hydrogen with the oxygenated hydrocarbons to generate the desired polyol, diol and/or alcohol product 215. Effluent stream 207 from the reactor contains a mixture of water, hydrogen, carbon dioxide, carbon monoxide, light hydrocarbons, light alcohols (methanol and ethanol), polyols, diols, ketones, aldehydes, carboxylic acids and unreacted glycerol.

The mixture is cooled and separated in a two-phase separator 208 where the non-condensable gases, such as hydrogen, carbon dioxide, carbon monoxide, methane, ethane and propane, are removed via stream 209 from the phase containing water-soluble polyols, alcohols and/or diols. The stream 209 can be either combusted to create process heat or sent to a separation system where hydrogen can be recovered for possible recycle back to stream 201 or used as a supplement 205.

Aqueous stream 210 is sent to a separator 211 where the light alcohols (methanol and ethanol) and water are removed and recycled back via stream 212 to the reactor inlet. A purge stream 217 is included to prevent a build-up of water in the reactor system. A crude product stream 213 containing the desired product 215 and unreacted feedstock is recovered from separator 211 via stream 213 and sent to a finishing separator 214 where the desired product 215 is separated from the unreacted feedstock 216. The unreacted feedstock stream is added to stream 216 and recycled back to the reactor system via stream 218 or used as supplement 205.

The following examples are included solely to provide a more complete disclosure of the subject invention. Thus, the following examples serve to illuminate the nature of the invention, but do not limit the scope of the invention disclosed and claimed herein in any fashion.

EXAMPLES

Example 1

A trimetallic catalyst system containing 5 wt % ruthenium, tin and platinum (molar ratio 1:1:0.5) supported on monoclinic zirconia was prepared using incipient wetness techniques. An aqueous solution with a volume equal to the incipient wetness volume for the zirconia to be impregnated, 19.45 mL, and containing 19.5 g of ruthenium nitrosylnitrate (Strem 1.5 g/mL Ru), 1.0 g of tin (IV) chloride hydrate (Alfa Aesar) and 0.7 g dihydrogen hexachloroplatinate (IV) hexahydrate (Alfa Aesar 39.51% Pt) was applied dropwise to 38.9 g of monoclinic zirconia while stirring. Seven sequential additions were required to obtain the 5 wt % ruthenium catalyst, drying the wetted zirconia at 110° C. and under vacuum following each addition of the metals. The catalyst was then calcined with air at a gradient temperature reaching 400° C.

over a period of 14 hours. Once the desired temperature was reached, the catalysts were further soaked in air for an additional 4 hours.

Example 2

A trimetallic catalyst system containing 5 wt % ruthenium, tin and rhenium (molar ratio 1:1:0.5) supported on monoclinic zirconia was prepared using incipient wetness techniques. An aqueous solution with a volume equal to the incipient wetness volume for the zirconia to be impregnated, 19.35 mL, and containing 19.4 g ruthenium nitrosylnitrate (Strem 1.5 g/mL Ru), 1.0 g tin (IV) chloride hydrate (Alfa Aesar) and 0.5 g perrhenic acid (Alfa Aesar 55.86 wt % Re) was applied dropwise to 38.7 g of monoclinic zirconia while stirring. Seven sequential additions were required to obtain the 5 wt % ruthenium catalyst, drying the wetted zirconia at 110° C. and under vacuum following each addition of the metals. The catalyst was then calcined with air at a gradient temperature reaching 400° C. over a period of 14 hours. Once the desired temperature was reached, the catalysts were further soaked in air for an additional 4 hours.

Example 3

A bimetallic catalyst system containing 5 wt % ruthenium and tin (molar ratio 1:1) supported on monoclinic zirconia was prepared using incipient wetness techniques. An aqueous solution with a volume equal to the incipient wetness volume for the zirconia to be impregnated, 10.4 mL, and containing 9.5 g ruthenium nitrosylnitrate (Strem 1.5 g/mL) and 0.5 g tin (IV) chloride hydrate (Alfa Aesar) was applied dropwise to 18.88 g monoclinic zirconia while stirring. Seven sequential additions were required to obtain the 5 wt % ruthenium catalyst, drying the wetted zirconia at 110° C. and under vacuum following each addition of the metals. The catalyst was then calcined with air at a gradient temperature reaching 400° C. over a period of 14 hours. Once the desired temperature was reached, the catalysts were further soaked in air for an additional 4 hours.

Example 4

The catalyst systems described in Examples 1, 2 and 3 above were tested to determine their performance in converting a feedstock solution containing 50 wt % glycerol to propylene glycol using external hydrogen. Prior to introducing the feedstock solution, the catalysts were each reduced with hydrogen flowing at a space velocity of 700 hr$^{-1}$, a 4 hour temperature gradient to 350° C., followed by a 2 hour hydrogen soak. The reactor system employed was a shell-in-tube reactor system as described in U.S. patent application Ser. No. 11/800,671 to Cortright et al., which is incorporated herein by reference. The reaction conditions were set at 220° C., 682 psig, and a weight hour space velocity (WHSV) of 1.0 grams glycerol per gram of catalyst per hour. The hydrogen was provided at an $H_2$/glycerol ratio of 2.46.

Figure 5:
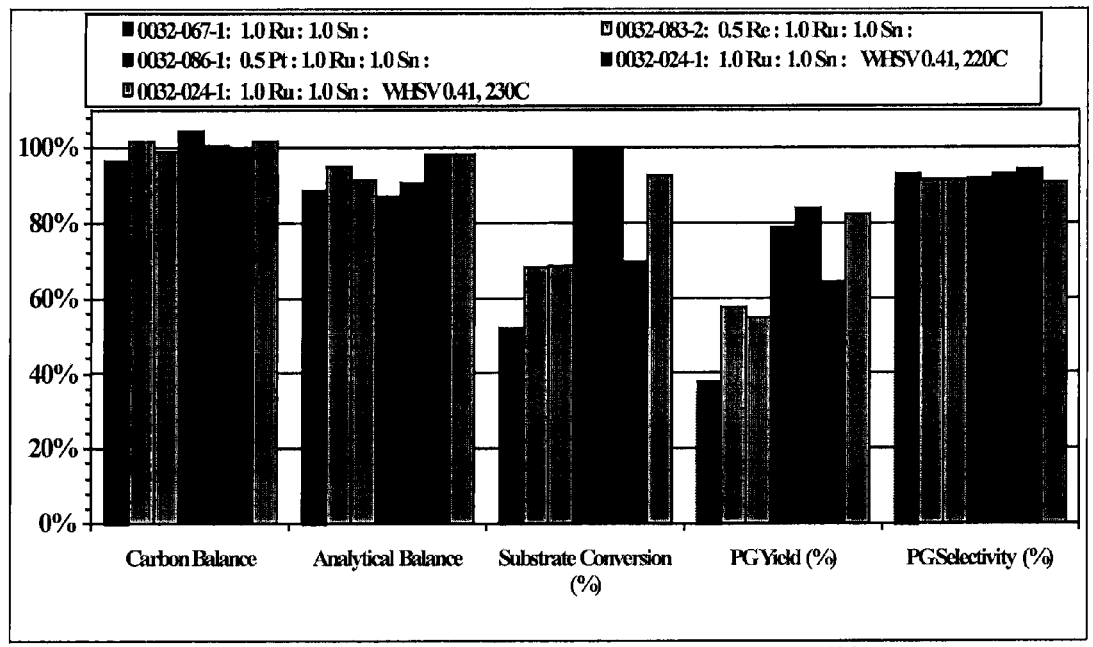
FIG. 5 is a chart reporting the catalytic performance of various catalysts in the conversion of glycerol to propylene glycol.
Figure 6:
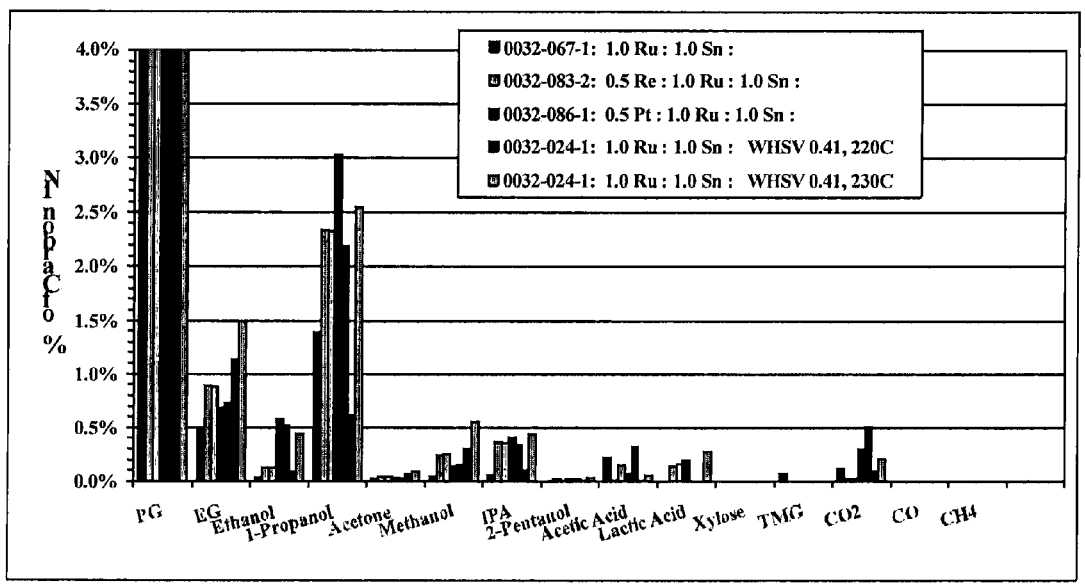
FIG. 6 is a chart reporting the selectivity of various catalysts in the conversion of glycerol to diols, alcohols, ketones, carboxylic acids, gases, and light hydrocarbons.

The results from feeding external hydrogen are shown in FIG. 5. The addition of rhenium increased the glycerol conversion from 52% to 68%. The addition of platinum increased the conversion to 100%. As the glycerol conversion increased, the PG selectivity remains effectively constant. The PG yield increased from 38% to 58% to 79% when going from Ru:Sn to Re:Ru:Sn to Pt:Ru:Sn, respectively. As illustrated in FIG. 6, the selectivity of by-products, such as EG, ethanol, n-propanol, and $CO_2$ increase as the glycerol conversion increased while switching from Ru:Sn to Re:Ru:Sn and Pt:Ru:Sn catalysts.

Figure 7:
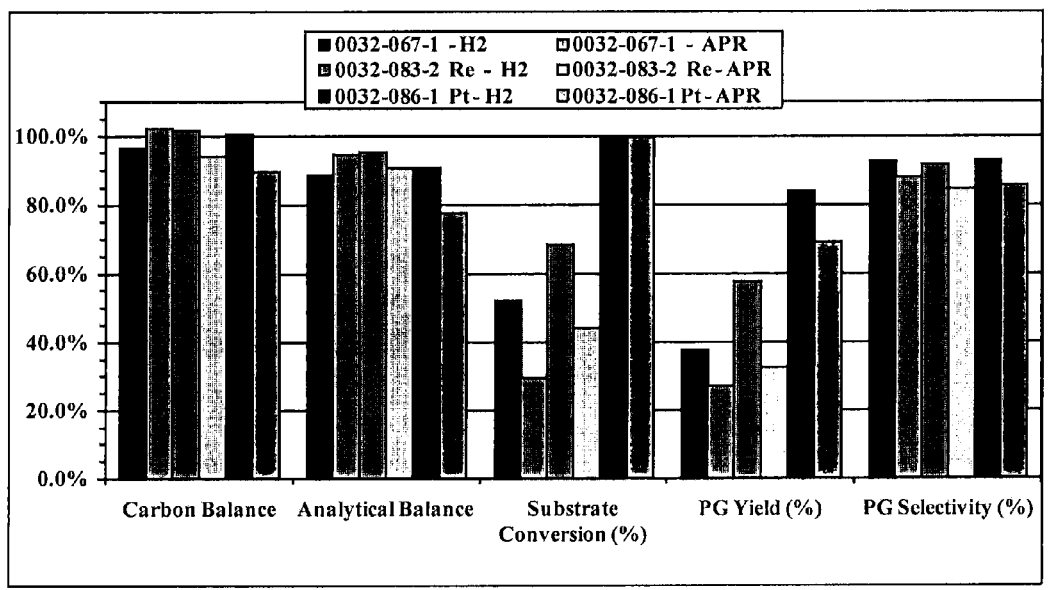
FIG. 7 is a chart reporting the catalytic performance of various catalysts in the conversion of glycerol to propylene glycol using external hydrogen and in situ generated APR hydrogen.

The high activity catalysts were tested with APR generated hydrogen to determine if the additional promoters decrease the impact of the APR hydrogen. The results in FIG. 7 show that the addition of platinum greatly reduces the negative impact of the APR generated hydrogen on the glycerol conversion and the PG yield is greatly increased compared to the Ru:Sn catalyst. The 70% PG yield with APR generated hydrogen is a remarkable and unexpected discovery and establishes the use of APR generated hydrogen in an integrated APR-HDO process. The addition of rhenium provided a slight improvement in the PG yield over the base Ru:Sn catalyst when the APR generated hydrogen was used.

Example 5

The Pt:Ru:Sn HDO catalyst of Example 1 was tested for its ability to produce propylene glycol from glycerol using in situ hydrogen generated through the aqueous phase reforming of glycerol in the vapor phase. The APR reactor was operated in upflow mode, with 5 wt % Pt Pt:Re 1:0.5 on Calgon 206P APR catalyst. Initial operation conditions for the aqueous phase reforming of glycerol to hydrogen was set at 400° C., 700 psig, a weight hour space velocity (WHSV) of 10 hr$^{-1}$, and a feed of 30 wt % glycerol.

All products from the APR reactor (e.g., hydrogen, carbon dioxide, carbon monoxide, water, etc.) were fed along with an aqueous feedstock solution containing 50 wt % glycerol to a trickle-bed HDO reactor containing the Pt:Ru:Sn HDO catalyst. The HDO reactor was operated with initial operating conditions of 220° C., 700 psig, and a WHSV of 2 hr$^{-1}$. The reactor configuration was set so that the gaseous products from the APR reactor co-currently mixed with the 50 wt % glycerol feed in a downflow mode.

The system was run at initial conditions for ten days to demonstrate operability and observe deactivation. After a baseline was established, process adjustments were made. The temperature of the HDO reactor was raised to increase glycerol conversion. The WHSV of the APR reactor was decreased to minimize glycerol usage for hydrogen production while still producing more than the stoichiometric amount needed for HDO. Finally, a hydrogen recycle was simulated for the HDO reactor by introducing a pure hydrogen stream into the HDO along with the APR feed.

Figure 8:
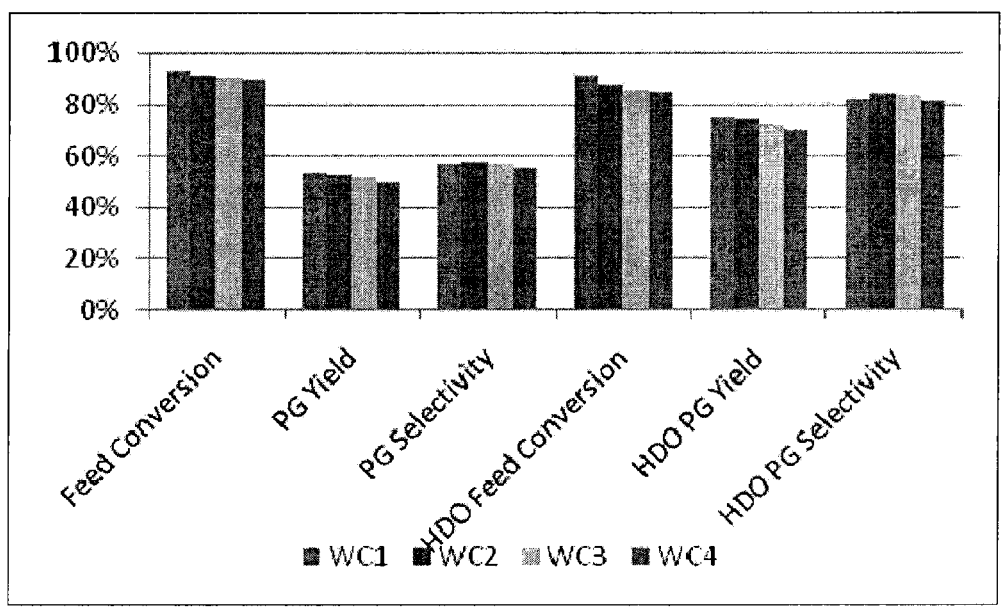
FIG. 8 is a chart providing conversion and yield data from the conversion of glycerol to propylene glycol in an APR-HDO reactor system employing a Pt:Ru:Sn HDO catalyst and a 5 wt % Pt Pt:Re 1:0.5 on Calgon 206P APR catalyst.

The initial performance of the APR-HDO system is shown in FIG. 8. Glycerol conversion was 91% and the system PG yield was 53%. Assuming complete glycerol conversion in the APR reactor, the HDO portion had a 75% PG yield with 82% selectivity. Complete conversion in the APR reactor was confirmed by collecting an aqueous sample from the midpoint of the two reactors. The sample had less than one half of a percent total organic carbon, indicating virtually complete glycerol feed conversion.

Figure 9:
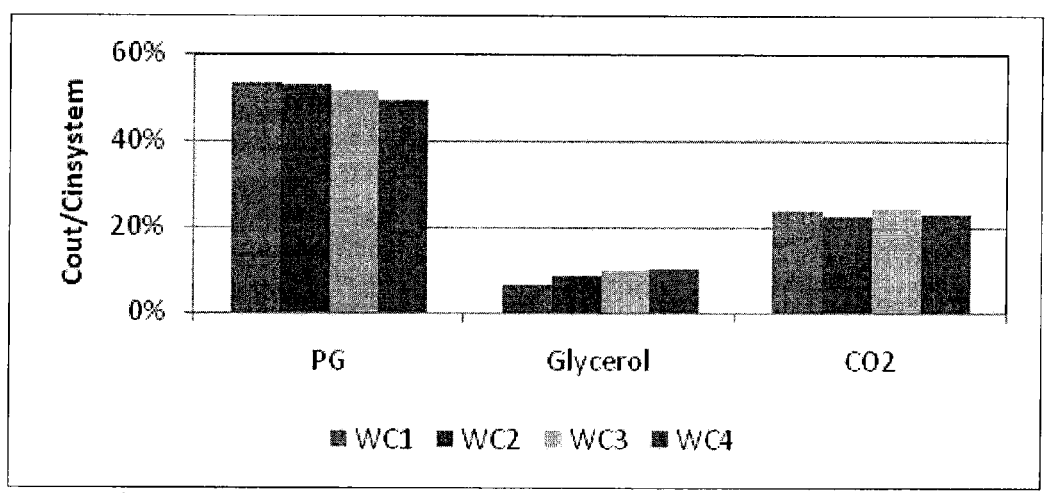
FIG. 9 is a chart providing the product distribution for the major components derived from the conversion of glycerol to propylene glycol in an APR-HDO reactor system employing a Pt:Ru:Sn HDO catalyst and a 5 wt % Pt Pt:Re 1:0.5 on Calgon 206P APR catalyst.
Figure 10:
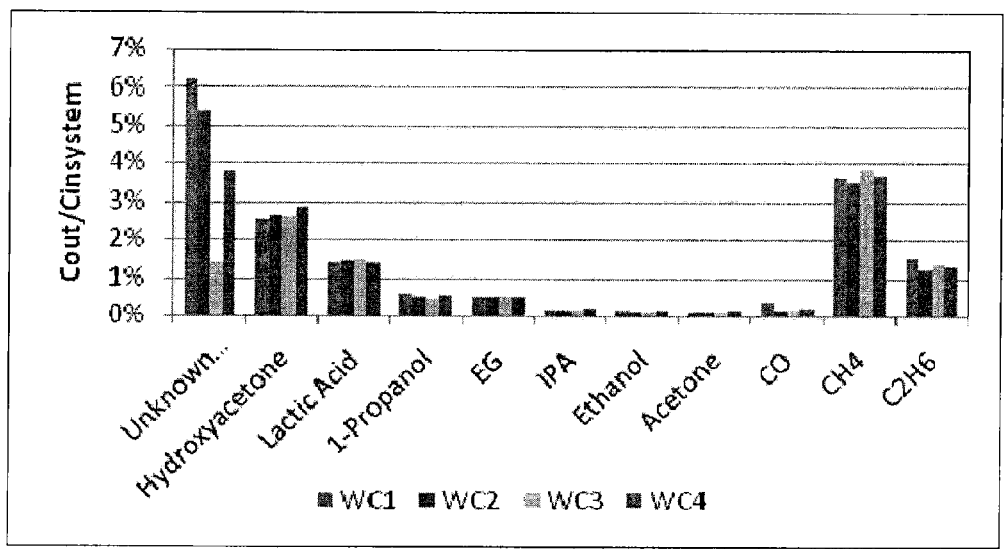
FIG. 10 is a chart providing the product distribution for the byproducts derived from the conversion of glycerol to propylene glycol in an APR-HDO reactor system employing a Pt:Ru:Sn HDO catalyst and a 5 wt % Pt Pt:Re 1:0.5 on Calgon 206P APR catalyst.

The product distribution for the system is in FIGS. 9 and 10. Major components are PG, unconverted glycerol, and carbon dioxide. Smaller byproducts include hydroxyacetone, lactic acid, propanol, methane, and unknowns. The amount of hydrogen produced, based on carbon dioxide exiting the system, was 0.26 mol $H_2$ out/mol C in, which was 83% of theoretical. This resulted in a 2.4:1 hydrogen to glycerol ratio in the HDO reactor. Approximately 54% of the hydrogen was consumed in the HDO reactor.

Example 6

A trimetallic catalyst system containing 2 wt % ruthenium, 1 wt % tin and 2 wt % platinum supported on tungstated zirconia (Norpro) was prepared using incipient wetness techniques. An aqueous solution with a volume equal to the incipient wetness volume for the zirconia to be impregnated, containing 1.02 g of ruthenium chloride (Aldrich), 0.60 g of tin chloride (Alfa Aesar) and 1.26 g dihydrogen hexachloroplatinate (IV) hexahydrate (Alfa Aesar 39.51% Pt) was applied dropwise to 25 g of tungstated zirconia while stirring. The wetted zirconia at 110° C. and under vacuum following each addition of the metals. The catalyst was dried for 4 hours at 120° C., then calcined with air at 1.6° C./min reaching 400° C. Once the desired temperature was reached, the catalyst was further soaked in air for an additional 4 hours.

The catalyst system described above was tested to determine its performance in converting a feedstock solution containing 50 wt % 43DE corn syrup to mono- and dioxygenates using external hydrogen. The 50 wt % 43 DE corn syrup was ion exchanged using a mixed bed resin. Prior to introducing the feedstock solution, the catalyst was reduced with hydrogen flowing at a space velocity of 1000 hr$^{-1}$, a two hour temperature gradient to 300° C., followed by a one hour hydrogen soak. The reactor system employed was a shell-in-tube reactor system as described in U.S. patent application Ser. No. 11/800,671 to Cortright et al., which is incorporated herein by reference. The reaction conditions were set at 1050 psig, a weight hour space velocity (WHSV) of 0.5 grams corn syrup per gram of catalyst per hour, and four zone furnace temperatures were set to 180° C., 200° C., 230° C., 255° C. from inlet to outlet of the reactor. The hydrogen was provided at an H$_2$/glucose molar ratio of 10.

Figure 11:
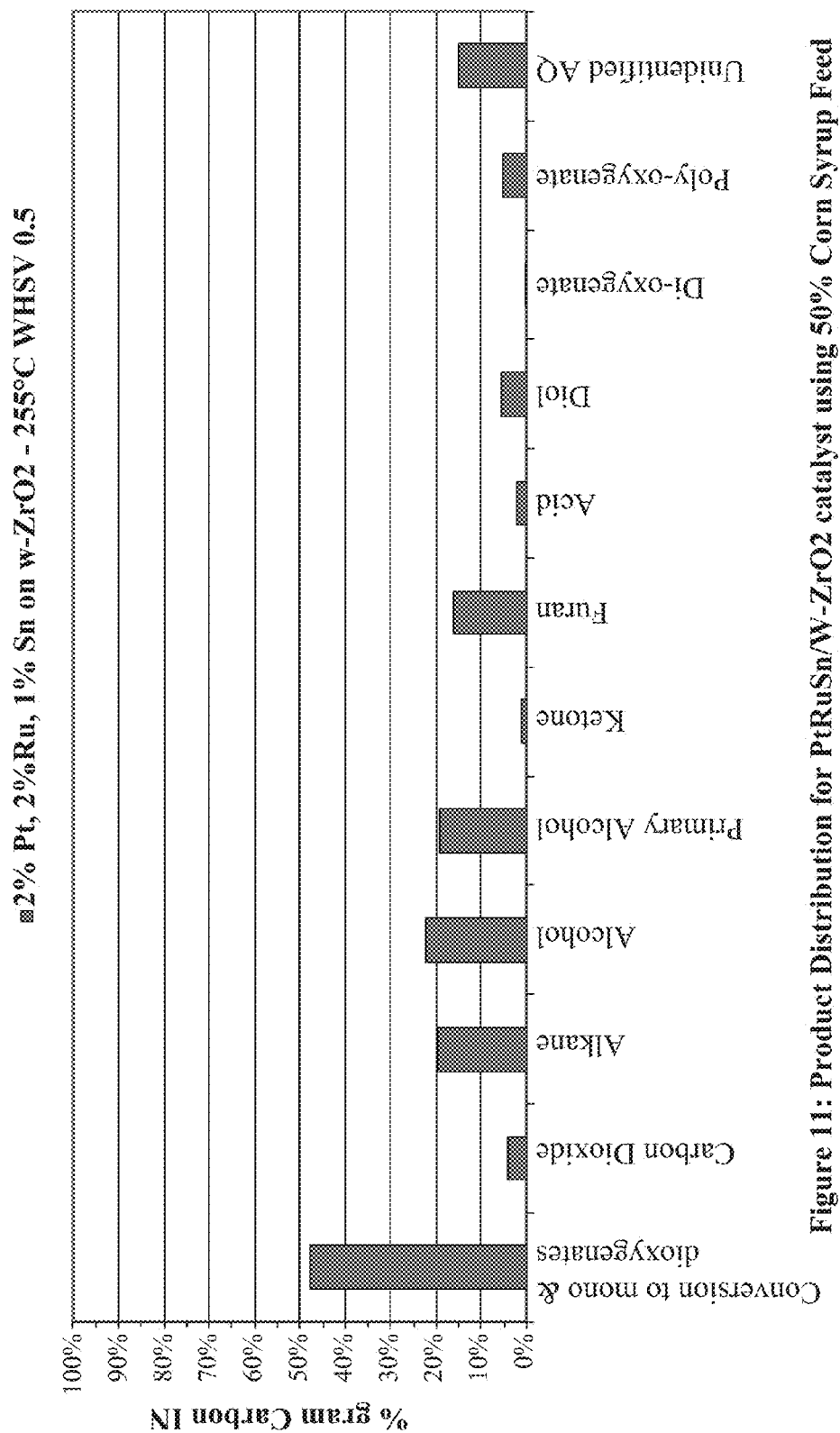
FIG. 11 is a chart providing the product distribution for the byproducts derived from the conversion of corn syrup to alcohols, ketones, carboxylic acids, furans, diols and polyols using a Pt:Ru:Sn HDO catalyst.

The results from feeding external hydrogen and corn syrup are shown in FIG. 11. The conversion of corn syrup to mono- and dioxygenates was 47.8% on a carbon basis. Alcohols, alkanes and furans were the most abundant species at 22.1%, 19.4%, and 16.3% respectively, as a percent of the carbon in. Of the alkanes produced, 77.8% were C5 or larger.

Although the Examples above only illustrate the effectiveness of the Pt:Ru:Sn HDO catalyst in converting glycerol and corn syrup to lower molecular weight products, it is expected that a similar efficiency in conversion and yields will also be achieved for other like feedstocks. This is because glycerol, sorbitol and other carbohydrates contain a hydroxyl group connected to a carbon and, regardless of carbon chain length, the chemistry of hydrodeoxygenation will not be dependent on the number of carbons within the compounds found in the feedstock.

We claim:

1. A method for converting oxygenated hydrocarbons to lower molecular weight oxygenated compounds, the method comprising the step of reacting an aqueous feedstock solution with hydrogen, at a temperature of between 100° C. and 300° C., in the presence of a heterogeneous catalyst, to produce a reaction product comprising one or more oxygenated compounds selected from the group consisting of a polyol, a ketone, an aldehyde, a carboxylic acid and an alcohol,
wherein the aqueous feedstock solution comprises water and one or more water soluble oxygenated hydrocarbons selected from the group consisting of a starch, a polysaccharide, a disaccharide, a monosaccharide, a polyhydric alcohol, a sugar, a sugar alcohol, and combinations thereof,
wherein the heterogeneous catalyst comprises ruthenium, platinum and tin, and wherein the oxygenated compound has a lower molecular weight than the oxygenated hydrocarbon.

2. The method of claim 1, wherein the heterogeneous catalyst contains greater than 0.1 wt % platinum, greater than 0.1 wt % ruthenium, and at least 0.1 wt % tin.

3. The method of claim 2, wherein the heterogeneous catalyst contains less than 6.0 wt % platinum, or less than 6.0 wt % ruthenium, or less than 6.0 wt % tin.

4. The method of claim 1, wherein the heterogeneous catalyst further comprises a support.

5. The method of claim 4, wherein the support is selected from the group consisting of carbon, silica, silica-alumina, alumina, zirconia, titania, tungsten, ceria, vanadia, oxides of the foregoing, and mixtures thereof.

6. The method of claim 1, wherein the hydrogen is generated by catalytically reacting a portion of the aqueous feedstock solution, at a temperature of between 80° C. and 400° C., and in the presence of an aqueous phase reforming catalyst comprising one or more Group VIII metals.

7. The method of claim 6, wherein the Group VIII metal is alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

8. The method of claim 1, wherein the hydrogen is generated by catalytically reacting a second aqueous feedstock solution comprising water and a second water-soluble oxygenated hydrocarbon having two or more carbon atoms, at a temperature of between 80° C. and 400° C., and in the presence of an aqueous phase reforming catalyst comprising one or more Group VIII metals.

9. The method of claim 8, wherein the Group VIII metal is alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

10. The method of claim 1, wherein the oxygenated hydrocarbon is selected from the group consisting of corn syrup, sucrose, glucose, fructose, maltose, lactose, mannose, xylose, arabitol, erythritol, glycerol, isomalt, lactitol, malitol, mannitol, sorbitol, xylitol, and alditol.

11. The method of claim 1, wherein the aqueous feedstock solution comprises at least 20 wt % glycerol.

12. The method of claim 1, wherein the reaction product has a propylene glycol yield of 40% or greater.

13. The method of claim 1, wherein the aqueous feedstock solution comprises at least 30 wt % corn syrup.

14. The method of claim 1, wherein the reaction product comprises propylene glycol and one or more of the following products: a second diol, a carboxylic acid, an aldehyde, and an alcohol.

15. A method of generating propylene glycol comprising the step of contacting a heterogeneous catalyst comprising platinum, ruthenium, and tin, with hydrogen and an aqueous feedstock solution comprising water and glycerol, at:
a) a temperature of about 200° C. to 280° C.;
b) a weight hourly space velocity of greater than 0.1 gram of glycerol per gram of the heterogeneous catalyst per hour; and
c) a pressure at which the water and the glycerol remain condensed liquids to produce a reaction product comprising propylene glycol.

16. The method of claim 15, wherein the method comprises at least one of the following:
a) the heterogeneous catalyst consists essentially of between 0.1 wt % and 6.0 wt % platinum, 0.1 wt % and 6.0 wt % ruthenium, 0.1 wt % and 6.0 wt % tin, on a zirconia support;
b) the feedstock comprises at least about 20 wt % glycerol;
c) the feedstock is contacted with the heterogeneous catalyst at a weight hourly space velocity of about 0.1 to 10.0 grams of glycerol per gram of the heterogeneous catalyst per hour and a pressure of about 625-700 psig; and d) the reaction product has a carbon yield of propylene glycol of 40% or greater.

17. The method of claim 15, wherein the hydrogen is generated by catalytically reacting a portion of the water and glycerol in the presence of an aqueous phase reforming catalyst comprising one or more Group VIII metals, at a temperature of between 80° C. and 300° C. and a pressure where the water and glycerol are condensed liquids.

18. The method of claim 17, wherein the Group VIII metal is alloyed or admixed with a member selected from the group consisting of Cu, B, Mn, Re, Cr, Mo, Bi, W, V, Nb, Ta, Ti, Zr, Y, La, Sc, Zn, Cd, Ag, Au, Sn, Ge, P, Al, Ga, In, Tl, Ce, alloys thereof, and combinations thereof.

* * * * *